(12) United States Patent
Kim et al.

(10) Patent No.: US 6,888,957 B1
(45) Date of Patent: May 3, 2005

(54) SYSTEM AND METHOD FOR DETECTING BLOBS ON AN END SURFACE OF AN OPTICAL FIBER

(75) Inventors: Wonoh Kim, Woodstock, MD (US); Darryl S. Ennels, Winsor Mill, MD (US)

(73) Assignee: CIENA Corporation, Linthicum, MD (US)

( * ) Notice: Subject to any disclaimer, the term of this patent is extended or adjusted under 35 U.S.C. 154(b) by 736 days.

(21) Appl. No.: 09/821,714

(22) Filed: Mar. 29, 2001

(51) Int. Cl.$^7$ .......................... G06K 9/00; G01N 21/00
(52) U.S. Cl. ..................................... 382/143; 356/73.1
(58) Field of Search ........................ 382/141, 143–151; 348/131; 356/71, 73.1, 341.1; 385/140, 97, 98, 99, 71; 427/163.2; 264/1.24, 1.25

(56) References Cited

U.S. PATENT DOCUMENTS

| | | | |
|---|---|---|---|
| 4,721,357 A | 1/1988 | Kovalchick et al. | 350/96.2 |
| 4,787,698 A | 11/1988 | Lyons et al. | 350/96.2 |
| 5,179,419 A | 1/1993 | Palmquist et al. | 356/73.1 |
| 5,651,083 A * | 7/1997 | Kortan et al. | 385/123 |
| 5,724,127 A | 3/1998 | Csipkes et al. | 356/73.1 |
| 5,729,622 A | 3/1998 | Csipkes et al. | 382/151 |
| 5,995,212 A | 11/1999 | Dar et al. | 356/73.1 |
| 2002/0109831 A1 * | 8/2002 | Van Nguyen et al. | 356/73.1 |

FOREIGN PATENT DOCUMENTS

JP 62299738 A 12/1987

OTHER PUBLICATIONS

ZX–1, "mini Zoom Interferometers", Direct Optical Research Company, Mar., 2001.
Cognex, "Machine Vision Solutions for the Fiber Optics Industry", OFC Booth 3838.
"Fiber–Optic Component Inspection Using Integrated Vision and Motion Components", National Instruments Corporation, Application Note 172, pp. 1–7, Feb., 2001.

* cited by examiner

*Primary Examiner*—Vikkram Bali
(74) *Attorney, Agent, or Firm*—Michael R. Commarala; David A. Fox

(57) ABSTRACT

An embodiment of the invention is a method for detecting defects in an optical fiber. The method includes obtaining an image of the optical fiber and separating a portion of the image for processing. A blob threshold is determined to isolate a blob in the portion of the image and characteristics of the portion of the image are adjusted to enhance detection of the blob. One or more blobs are detected in the image and a characteristic of the detected blobs is compared to blob criteria. The optical fiber is failed if the blob criteria are not met.

29 Claims, 10 Drawing Sheets

SYSTEM AND METHOD FOR DETECTING BLOBS ON AN END SURFACE OF AN OPTICAL FIBER

BACKGROUND

1. Field of Invention

The invention is directed generally to a system and method for inspecting an end surface of an optical fiber and particularly to automatic inspection to detect defects on the end surface of the optical fiber.

2. Description of Related Art

Optical fibers are widely employed to transmit light for many applications. In order to insure good performance of the optical fiber, the end surface of the optical fiber needs to be relatively free of defects. Typically, two optical fibers are joined at respective end surfaces. The presence of such defects in the optical fiber, particularly in the core region, may result in degraded performance such as increased insertion loss or poor return loss.

Automated inspection systems for optical fibers are known in the art. One exemplary automated inspection system is disclosed in U.S. Pat. No. 5,995,212, commonly owned by the assignee of this application and incorporated herein by reference in its entirety. U.S. Pat. No. 5,995,212 discloses an automated inspection system that detects defects in the core and cladding zones of the optical fiber and determines if the optical fiber meets certain standards. While the system and methods disclosed in U.S. Pat. No. 5,995,212 are well suited for their intended purpose, improvements to such systems are needed.

SUMMARY OF THE INVENTION

An embodiment of the invention is a method for detecting defects in an optical fiber. The method includes obtaining an image of the optical fiber and separating a portion of the image for processing. A blob threshold is determined to isolate a blob in the portion of the image and characteristics of the portion of the image are adjusted to enhance detection of the blob. One or more blobs are detected in the image and a characteristic of the detected blobs is compared to blob criteria. The optical fiber is failed if the blob criteria are not met. An alternate embodiment detects scratches on the optical fiber. Yet another embodiment is directed to a system of networked optical fiber inspection systems.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE INVENTION

The following detailed description of the invention refers to the accompanying drawings. The same reference numbers in different drawings identify the same or similar elements. Also, the following detailed description does not limit the invention. Instead, the scope of the invention is defined by the appended claims and equivalents thereof.

Figure 1:
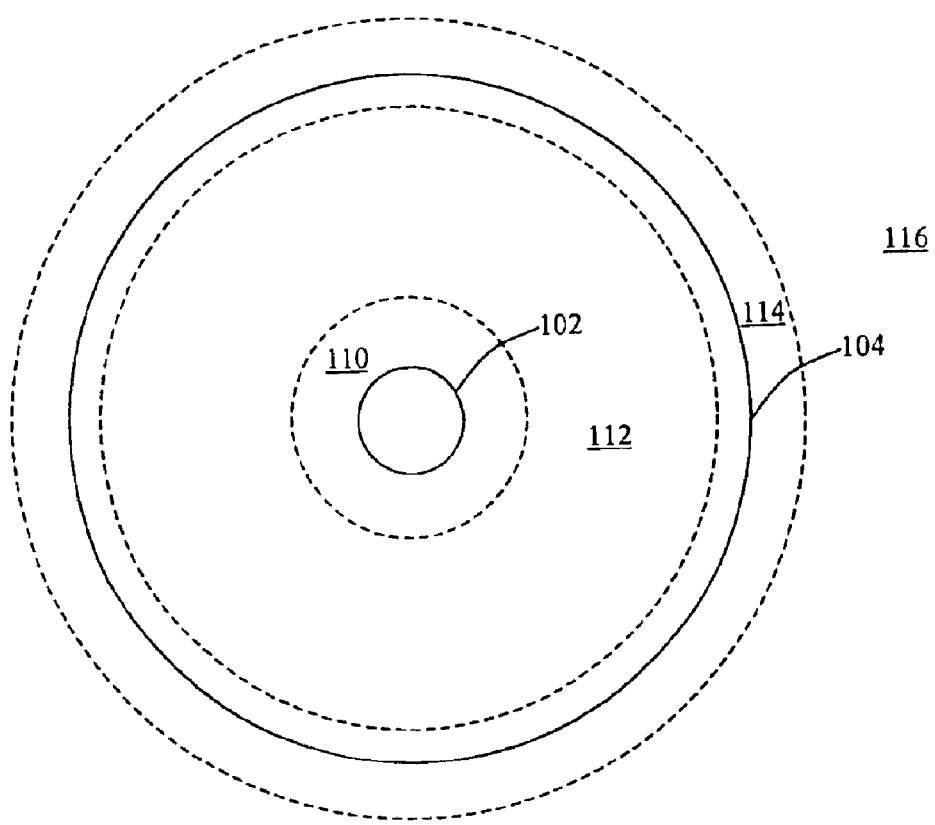
FIG. 1 is a cross-section of an optical fiber in a ferrule.

FIG. 1 is a cross-section of an optical fiber depicting a number of inspection zones. The optical fiber includes a core 102 surrounded by a cladding 104. Both the core 102 and the cladding 104 may be manufactured out of glass. The core 102 is typically very small, e.g., about four to nine microns in diameter for a single mode fiber. The cladding 104 typically has a larger diameter than the core region, e.g., about 125 microns in diameter. The cladding 104 may be surrounded by a supporting structure (e.g., a ferrule) that protects the core 102 and the cladding 104 from damage. The supporting structure may be, for example, a ferrule of approximately 2500 microns in diameter. The supporting structure may be attached to the cladding 104 by an epoxy layer.

Four inspection zones are defined, namely a core inspection zone 110, cladding inspection zone 112, fiber edge inspection zone 114 and supporting structure inspection zone 116. The core inspection zone 110 is slightly larger than core 102. The cladding inspection zone 112 covers the majority of the cladding 104. The fiber edge inspection zone 114 covers a portion of the cladding and adjoining areas such as the epoxy area. Lastly, the supporting structure inspection zone 116 covers all regions outside the fiber edge zone 114. As described in further detail herein, certain inspection zones can tolerate more defects and thus different quality requirements may be imposed for each inspection zone.

Figure 2:
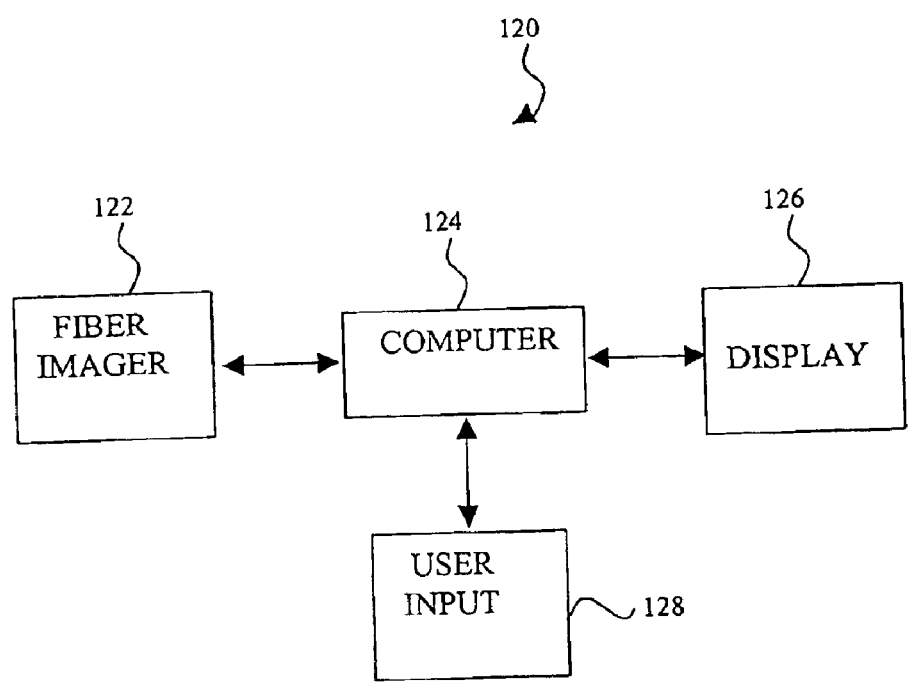
FIG. 2 is a schematic diagram of an inspection system in accordance with the present invention.

FIG. 2 is a schematic illustration of an embodiment of a system 120 used to perform the inspection in accordance with the present invention. The system 120 includes a fiber imager 122, a computer 124, a display 126 and a user input 128. The fiber imager 122 illuminates the fiber to be inspected and captures an image of the illuminated fiber. The fiber imager 122 may be implemented using known devices such as charge coupled devices (CCD's). In an embodiment of the invention, the fiber imager 122 is an FBP-P1 probe available from Westover Scientific that includes a CCD, light source and associated optical elements.

The fiber imager 122 provides an image of the optical fiber to the computer 124, which stores and processes the image to determine the presence of defects as described in further detail herein. The computer 124 displays this image on the display 126. The image may be made up of an array of picture elements (pixels) which typically vary in intensity from 0, representing black, to 255, representing white. The user input 128 may be used to provide information regarding the fiber to be inspected, to begin testing, etc.

Figure 3A:
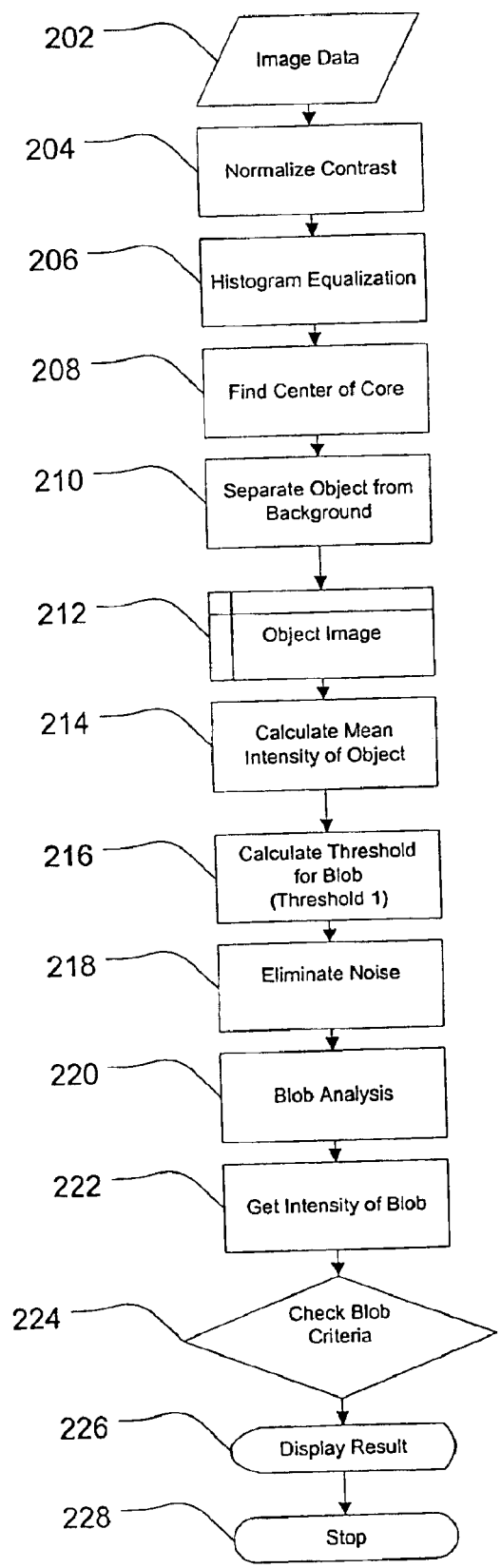
FIGS. 3A–3D are flowcharts of a process for inspecting an optical fiber for defects.
Figure 3B:
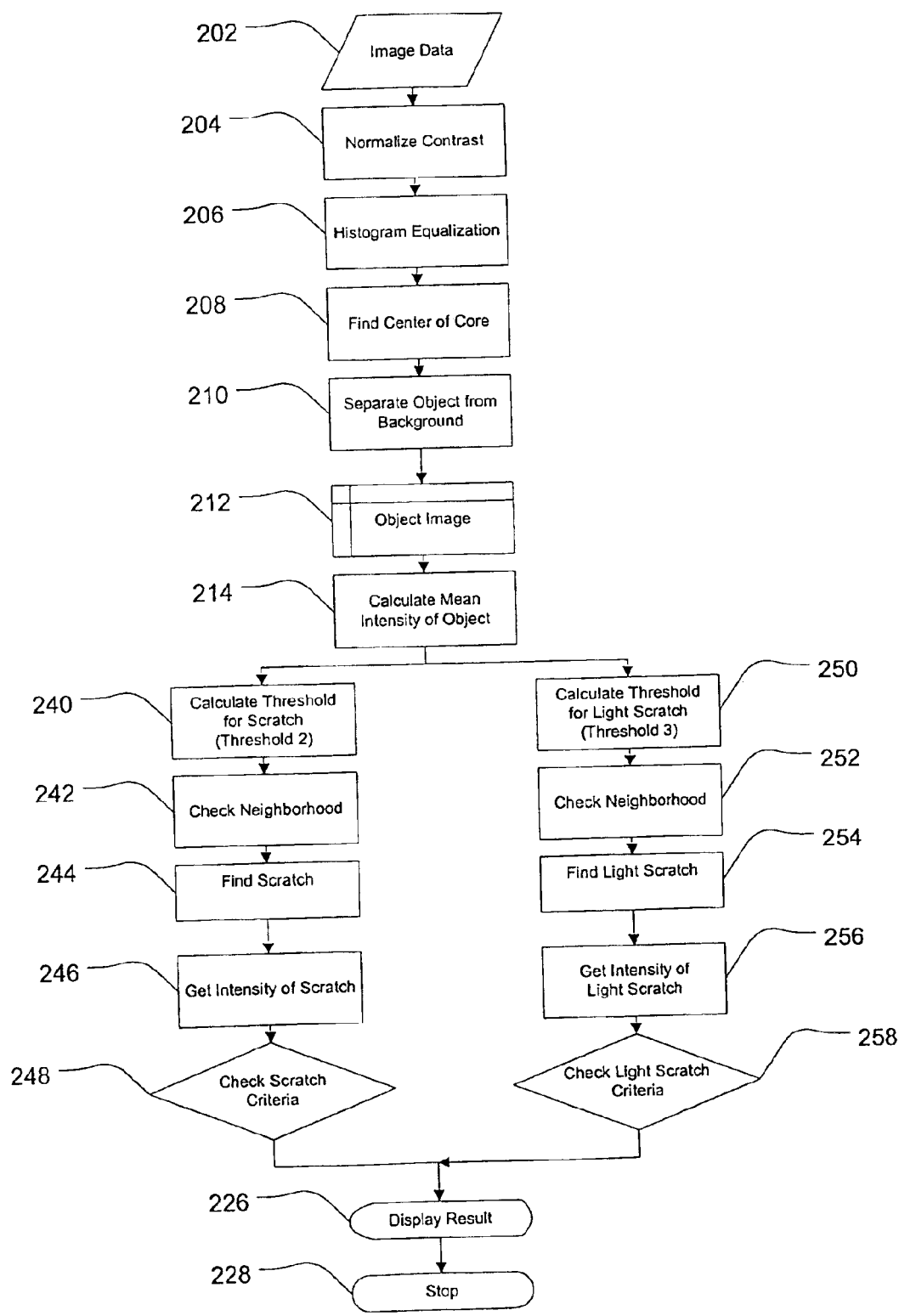
Figure 3C:
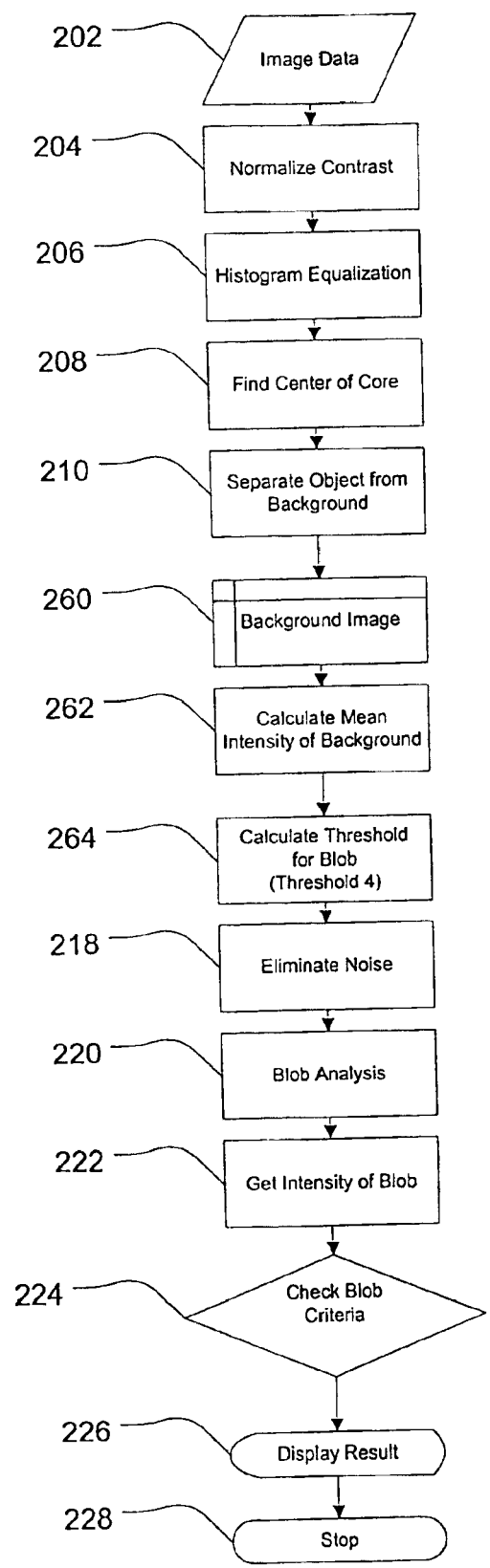
Figure 3D:
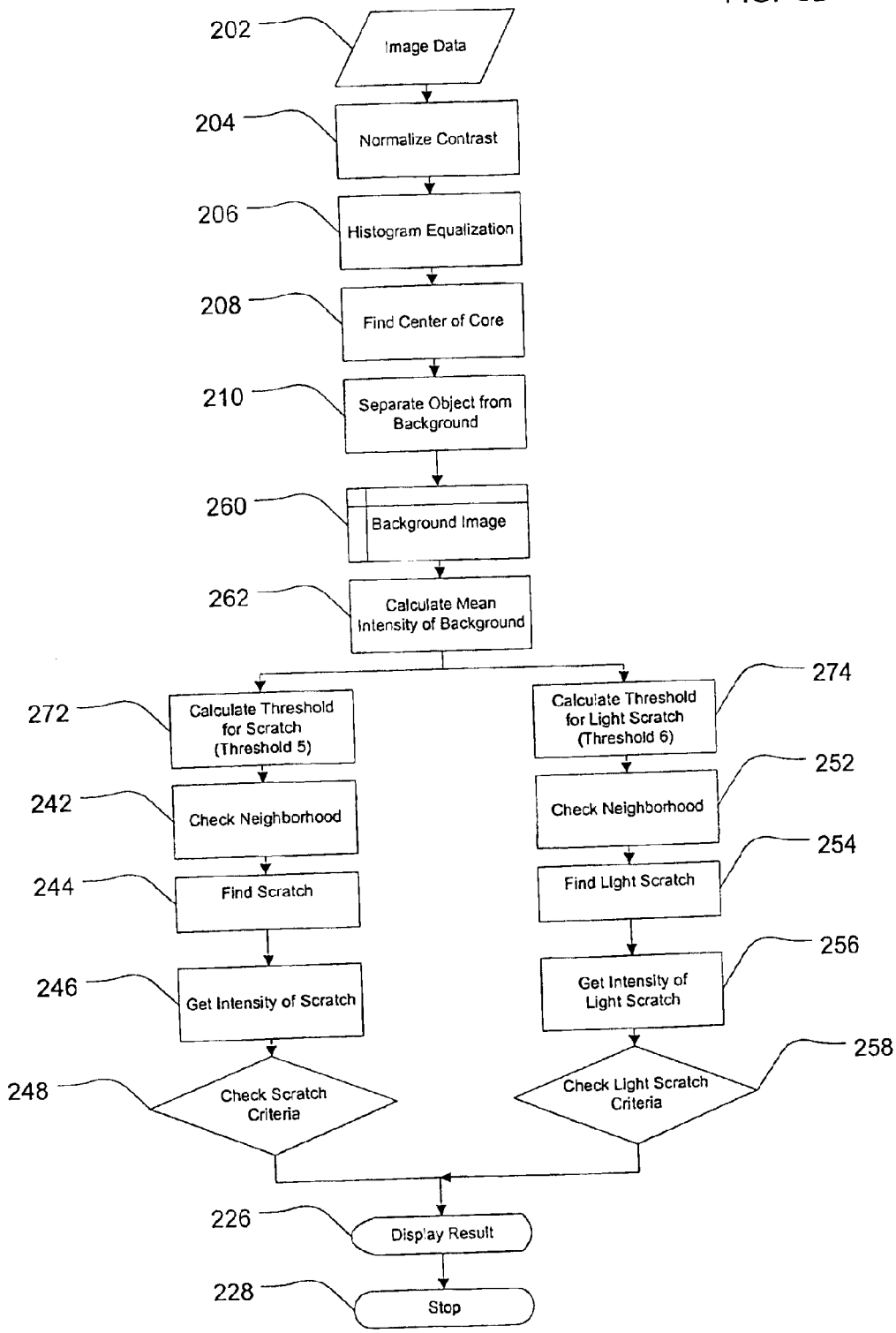

FIGS. 3A–3D are flowcharts of processing performed by system 120 to inspect optical fibers. The processing detects blobs in the object portion (e.g., core/cladding) as shown in FIG. 3A, scratches in the object portion as shown in FIG. 3B, blobs in the background portion (e.g., ferrule) as shown in FIG. 3C and scratches in the background portion as shown in FIG. 3D. The terms "blob" and "scratch" are intended to have broad meanings with blob generally referring to spot defects (e.g., pits, chips) and scratch generally referring the defects traversing a path. Although each process is described individually, the processes may run concurrently and no order of processing is intended by the arrangement of FIGS. 3A–3D.

Referring to FIG. 3A, the object blob processing begins at step 202 by acquiring an original image of the end of the fiber and supporting structure. The original image may be obtained directly from fiber imager 122 or obtained from a storage device. The original image may be a gray scale image having pixel intensities ranging from 0 to 255.

At step 204, contrast of the original image is normalized to establish a predefined contrast for the image and accommodate for variations in brightness. At step 206, histogram equalization is performed to enhance contrast between features in the image. As known in the art, histogram equalization reassigns gray scale intensities in the image to distribute the histogram over a wider range of gray scale values. Equalizing the histogram provides a wider range over which to establish thresholds and thus reduces sensitivity of the threshold. At step 208 the center of the core 102 is located using known techniques. The location of the center of the core is used to define the object (e.g., core/cladding) and the background (e.g., ferrule). In addition, the core inspection zone 110, cladding inspection zone 112, fiber edge inspection zone 114 and supporting structure inspection zone 116 are defined in the original image.

At step 210, the object is separated from the background to establish an object image 212. Thus, the object image contains the gray scale intensities from the processed original image (i.e., original image after contrast normalization and histogram equalization). The object image 212 represents, for example, the core/cladding region and is processed to detect blobs as shown in FIG. 3A and scratches as shown in FIG. 3B.

Once the object image 212 is defined, the mean intensity of the object is determined at step 214. The mean object intensity is used to establish an object blob threshold as described herein. In an exemplary embodiment, blobs are detected in the object region and excluded from the determination of the mean object intensity.

Once the mean object intensity is determined, an object blob threshold is set at step 216. The object blob threshold may be a function of the mean object intensity determined in step 214. In an exemplary embodiment, the object blob threshold is computed as $$T_{OB} = \alpha_1 \times I_O \beta_1$$

where $T_{OB}$ is the object blob threshold, $I_O$ is the mean object intensity and $\alpha_1$ and $\beta_1$ are scaling constants. Test parameters may be adjusted prior to applying the threshold so that detection of blobs is enhanced. In an exemplary embodiment, the brightness is set to a low value and the contrast is set to a medium value prior to applying the object blob threshold. These test parameters are selected to help distinguish the blobs from the object. Due to variance in imaging characteristics from one optical fiber inspection system to the next, the test parameters (e.g., brightness and/or contrast) may be tuned for each optical fiber inspection system. Causes for such variance may include variance in camera sensitivity, variance in lighting, etc. The brightness and contrast are adjusted or tuned to compensate for variance in imaging characteristics and enhance detection of blobs. The test parameters may also be stored and managed centrally in a networked system as described herein with reference to FIG. 7.

Figure 4:
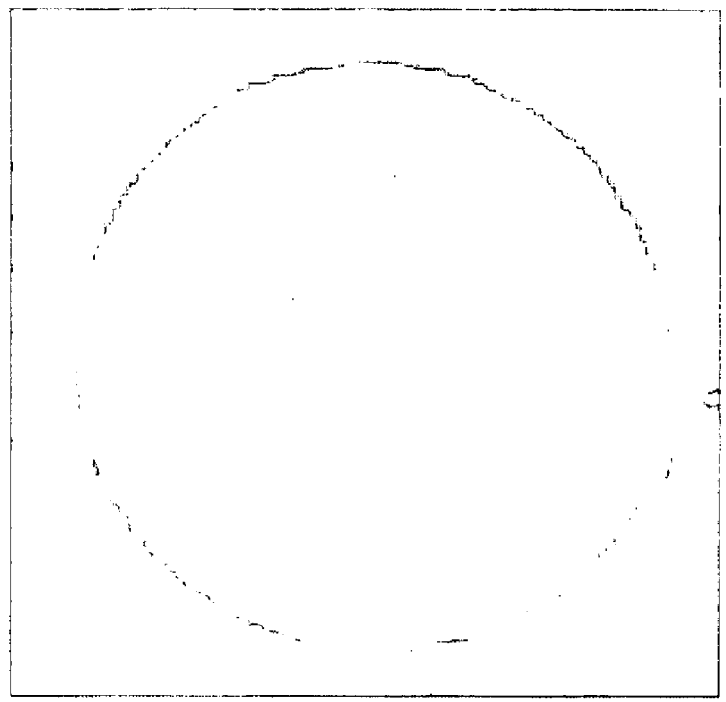
FIG. 4 depicts and exemplary original image.
Figure 5:
FIG. 5 depicts an exemplary binary object image processed for detecting blobs.

The object blob threshold is applied and the object image is converted to a binary object image. FIG. 4 depicts an exemplary original image and FIG. 5 depicts an exemplary binary blob image derived from the original image. As shown in FIG. 5, the binary blob image may be displayed along with blob intensities derived from the original image as described herein.

An alternate thresholding technique involves the use of a fuzzy thresholding routine. The fuzzy thresholding process includes using fuzzy membership sets to assign brightness indicators to areas of the image. The background (e.g., ferrule) may be considered LIGHT WHITE and blobs in the background LIGHT GRAY. The object (e.g., core/cladding) may be considered LIGHT BLACK and a blob on the object DARK GRAY. Thresholds are then set to separate the background from the background blobs and to separate the object from the object blobs.

At step 218, the binary object image is processed to remove noise which can improperly be detected as blobs. One technique for such noise elimination is morphological filtering. Other noise reduction techniques such as a moving average kernel may used at step 218.

Once the noise is eliminated, flow proceeds to step 220 where blob analysis is performed. The binary object image is processed to detect the presence and size of blobs. Such processing may be performed using known techniques such as those described in U.S. Pat. No. 5,995,212. Briefly, such techniques involve locating regions having intensities deviating from a local average intensity by a predetermined amount. Size constraints may be applied to prevent noise (not eliminated at step 218) and scratches from being considered blobs. The locations and sizes of all blobs are recorded.

Once blobs have been detected in the binary object image, the intensity for each blob is determined from the processed original image. As noted above, the location of each blob in the binary object image is recorded and used to locate corresponding pixels in the processed original image (i.e., original image after contrast normalization and histogram equalization). The intensity (e.g., gray scale value) of the blob is determined at step 222. The intensity of the blob may be based on a statistical function such as the average intensity or median intensity of pixels making up the blob. Once the blob intensities and sizes are determined, flow proceeds to step 224 where it is determined whether blob criteria are met. Exemplary blob criteria are set forth in Table 1.

TABLE 1

|  | Core Region | Cladding Region | Fiber Edge Region | Ferrule Region |
| --- | --- | --- | --- | --- |
| Blob | none allowed | <5 um blobs allowed | <10 um blobs allowed | any number of blobs allowed |
| Scratch | none | <3 scratches of any size allowed | any number of scratches allowed | any number of scratches allowed |
| Contamination | none | None | None | none |

As show in Table 1, the core inspection zone 110 can have no blobs, the cladding inspection zone 112 may have blobs that are less than 5 microns in size, the fiber edge inspection zone 114 may have blobs that are less than 10 microns in size and the supporting structure inspection zone 116 may have any number of blobs. If the blob criteria are not met at step 224, then the optical fiber is failed. The user is notified of the result at step 226 and the object blob processing ends at step 228.

The blob criteria applied at step 224 may also be dependent on the intensity of the blobs. As noted above, the intensity of each blob is determined at step 222. Blob criteria may then be based on blob intensity. For example, the cladding inspection zone may be permitted to have up to 10 gray blobs and up to 5 black blobs where parameters such as gray and black are defined by gray scale intensity ranges.

FIG. 3B depicts object scratch processing used to detect scratches on the object (e.g., core/cladding). The processing performed through steps 202–214 is the same in FIG. 3B as that shown in FIG. 3A. Once the mean object intensity is determined at 214, two scratch detection processes are performed. A first scratch detection process is implemented through steps 240–248 for detecting dark scratches and a second scratch detection process is implemented through steps 250–258 for detecting light scratches. A light scratch is a scratch having an intensity close to the intensity of the underlying surface, be it the object (e.g., core/cladding) or background (e.g., ferrule). Such light scratches may be overlooked by scratch processing because the threshold set for scratches may not capture light scratches. Thus, separate light scratch detection is performed.

Figure 6:
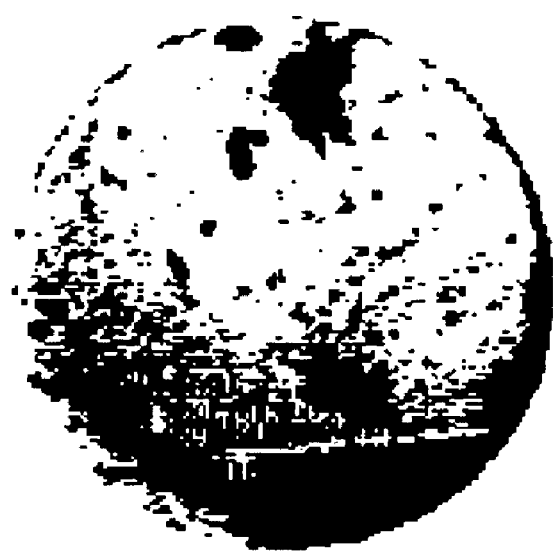
FIG. 6 depicts an exemplary binary object image processed for detecting scratches.

At step 240, an object scratch threshold is set. The object scratch threshold may be a function of the mean object intensity determined in step 214. In an exemplary embodiment, the object scratch threshold is computed as $$T_{OS} = \alpha_2 \times I_O - \beta_2$$

where $T_{OS}$ is the object scratch threshold, $I_O$ is the mean object intensity and $\alpha_2$ and $\beta_2$ are scaling constants. Test parameters may be adjusted prior to applying the object scratch threshold so that detection of scratches is enhanced. In an exemplary embodiment, the brightness is set to a medium value and the contrast is set to a high value prior to applying the object scratch threshold. These test parameters are selected to help distinguish the scratches from the object. In addition, the test parameters may also compensate for variance in imaging characteristics as described above. The object scratch threshold is applied and the object image is converted to a binary object image. FIG. 6 depicts an exemplary binary object image derived from the original image in FIG. 4 using the object scratch threshold.

At step 242, the binary object image is processed to determine if a group of isolated blobs actually define a scratch. Morphological filtering may be used to determine the connectivity of a series of blobs. Morphological filtering may include dilating pixel regions so that adjacent isolated defects become morphologically connected. If it is determined if several blobs are morphologically connected consecutively along a continuous path (either linear or curved), in a length exceeding a scratch size threshold, then this group of blobs is linked to define a continuous defect.

At step 244, the binary object image is processed to detect the presence and size of scratches. The scratch detection may be performed using known techniques such as those described in U.S. Pat. No. 5,995,212. Briefly, such techniques may involve locating edge pixels in the image and performing a Hough transform to confirm the presence of valid scratches. A size threshold may be applied to so that a predetermined minimum length scratch length is met to prevent blobs from being classified as scratches. Alternate scratch detection techniques may be used such as processing the image with a gradient kernel to detect magnitude and orientation of edge pixels in the images. Proximate edge pixels having common orientations may be classified as a single scratch. The locations and sizes of all scratches are recorded.

Once scratches have been detected in the binary object image, the intensity of each scratch is determined from the original image. As noted above, the location of each scratch in the binary object image is recorded and used to locate corresponding pixels in the processed original image. The intensity (e.g., gray scale value) of the scratch is determined at step 246. The intensity of the scratch may be based on a statistical function such as the average intensity or median intensity of pixels making up the scratch. Once the scratch intensities and sizes are determined, flow proceeds to step 248 where it is determined whether scratch criteria are met. Exemplary scratch criteria are set forth in Table 1. The results are displayed to the user at step 226 and the processing ends at step 228.

As described above with respect to object blobs, the scratch criteria applied at step 248 may also be dependent on the intensity of the scratches. As noted above, the intensity of each scratch is determined at step 246. Scratch criteria may then be based on scratch intensity. For example, the cladding inspection zone may be permitted to have up to 3 gray scratches and 1 black scratch where parameters such as gray and black are defined by gray scale intensity ranges.

In addition to scratch detection performed at steps 240–248, detection of light scratches is performed at steps 250–258. The light scratch processing is similar to the scratch processing with step 250 being the primary difference. The light scratches usually are difficult to distinguish from the neighborhood pixels. Thus, the object light scratch threshold is calculated not only based on the underlying surface but also based on the mean intensity of blobs on the object. The mean intensity of blobs on the object is determined as described in FIG. 3A.

In an exemplary embodiment, the object light scratch threshold is computed as $$I_{OLS} = \alpha_3 \times I_O + \gamma_3 I_{Blob} + \beta_3$$

where $T_{OLS}$ is the object light scratch threshold, $I_O$ is the mean object intensity, $I_{Blob}$ is the mean intensity of the blobs on the object and $\alpha_3$, $\gamma_3$ and $\beta_3$ are scaling constants. Test parameters may be adjusted prior to applying the object light scratch threshold so that detection of light scratches is enhanced. In an exemplary embodiment, the brightness is set to a medium value and the contrast is set to a high value prior to applying the object light scratch threshold. These test parameters are selected to help distinguish the light scratches from the object. In addition, the test parameters may also compensate for variance in imaging characteristics as described above. The object light scratch threshold is applied and the object image is converted to a binary object image.

Once the object light scratch threshold is applied at step 250, processing performed in steps 252–258 mirrors that in steps 242–248.

FIG. 3C depicts blob processing performed on the background portion (e.g., ferrule) in the original image. The processing performed on the background is similar to that shown in FIG. 3A and thus description of similar steps is omitted. The primary difference in FIG. 3C is the establishment of a background image 260 rather than an object image 212. The background image 260 corresponds to the portion of the processed original image outside the object (e.g., core/cladding). Once the background image 260 is defined, the mean intensity of the background is determined at step 262. The mean background intensity is used to establish a background blob threshold as described herein. In an exemplary embodiment, blobs are detected in the background region and excluded from the determination of the mean background intensity.

Once the mean background intensity is determined, a background blob threshold is set at step 264. The background blob threshold may be a function of the mean background intensity determined in step 262. In an exemplary embodiment, the background blob threshold is computed as $$T_{BB}=\alpha_4 \times I_B+\beta_4$$

where $T_{BB}$ is the background blob threshold, $I_B$ is the mean background intensity and $\alpha_4$ and $\beta_4$ are scaling constants. Test parameters maybe adjusted prior to applying the threshold so that detection of blobs is enhanced. In an exemplary embodiment, the brightness is set to a low value and the contrast is set to a medium value prior to applying the threshold. These test parameters are selected to help distinguish the blobs from the background. In addition, the test parameters may also compensate for variance in imaging characteristics as described above. The background blob threshold is applied and the background image is converted to a binary background image. The detection of blobs and determining if blob criteria are met are performed though steps 218–224 as described with reference to FIG. 3A.

FIG. 3D depicts scratch processing performed on the background portion (e.g., ferrule) in the original image. The processing performed on the background is similar to that shown in FIGS. 3B and 3C and thus description of identical steps is omitted. Different thresholds may used as exhibited at steps 272 and 274. A background scratch threshold is established at step 272. In an exemplary embodiment, the background scratch threshold is computed as $$T_{BS}=\alpha_5 \times I_B+\beta_5$$

where $T_{BS}$ is the background scratch threshold, $I_B$ is the mean background intensity and $\alpha_5$ and $\beta_5$ are scaling constants. Test parameters may be adjusted prior to applying the background scratch threshold so that detection of scratches is enhanced. In an exemplary embodiment, the brightness is set to a medium value and the contrast is set to a high value prior to applying the background scratch threshold. These test parameters are selected to help distinguish the scratches from the background. In addition, the test parameters may also compensate for variance in imaging characteristics as described above. The background scratch threshold is applied and the background image is converted to a binary background image. Processing of the background binary image is performed through steps 242–248 as described above with reference to FIG. 3B.

Similarly, the background light scratch threshold is established at step 274. In an exemplary embodiment, the background light scratch threshold is computed as $$T_{BLS}=\alpha_6 \times I_B+\gamma_6 \times I_{Blob}+\beta_6$$

where $T_{BLS}$ is the background light scratch threshold, $I_B$ is the mean background intensity, $I_{Blob}$ is the mean intensity of the blobs on the background and $\alpha_6$, $\gamma_6$ and $\beta_6$ are scaling constants. The mean intensity of blobs on the background is determined as described in FIG. 3C. Test parameters may be adjusted prior to applying the background light scratch threshold so that detection of scratches is enhanced. In an exemplary embodiment, the brightness is set to a medium value and the contrast is set to a high value prior to applying the background light scratch threshold. These test parameters are selected to help distinguish the light scratches from the background. In addition, the test parameters may also compensate for variance in imaging characteristics as described above. The background light scratch threshold is applied and the background image is converted to a binary background image. Processing of the background binary image is performed through steps 252–258 as described above with reference to FIG. 3B.

As described above, the object blob processing, object scratch processing, object light scratch processing, background blob processing, background scratch processing and background light scratch processing may occur concurrently. The results displayed at step 226 may include the results of all or one of the processes described. Thus, no order of processing is suggested by the arrangement of the figures.

Figure 7:
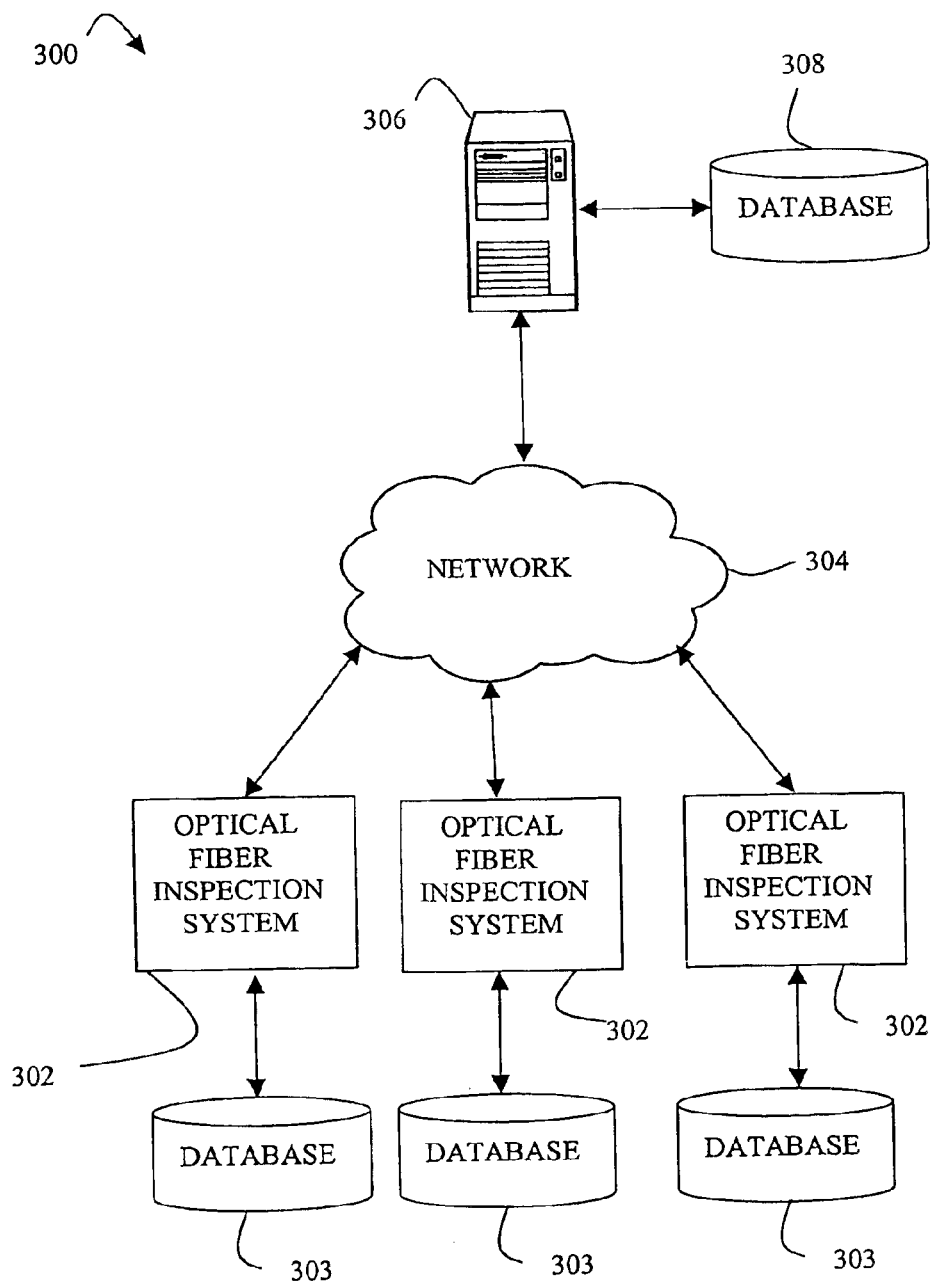
FIG. 7 is a diagram of a networked system of multiple optical fiber inspection systems.

FIG. 7 is a block diagram of a system 300 including a number of optical fiber inspection systems 302. Each of the optical fiber inspection systems 302 may be implemented using a system such as that shown in FIG. 1. Each optical fiber inspection system 302 is coupled to a network 304. Each computer 124 may include a network connection such as an Ethernet card. Network 304 may be any type of communication network including LAN, WAN, intranet, Internet, etc. Also coupled to the network 304 is a server 306. The server 306 has access to a database 308 which may be memory in server 306 or a separate device accessible by server 306.

The system of FIG. 7 allows test parameters for each optical fiber inspection system 302 to be updated by server 306. As described above, test parameters such as brightness and contrast are tuned during the inspection process. Database 308 may also store test results from each of the optical fiber inspection systems 302 in addition to the test parameters. Test parameters such as brightness and contrast controls can be distributed from server 306 to the optical fiber inspection systems 302. This may be helpful when inspecting a particular optical fiber assembly. The optical fiber inspection system 302 can download the appropriate test parameters developed for that assembly in order to tune the optical fiber inspection system 302.

Each optical inspection system 302 may have certain characteristics that require test parameters (e.g., brightness or contrast settings) to vary from system to system. As described above, the brightness and/or contrast are often tuned to accommodate imaging characteristics and/or to detect a particular type of defect. Storing test parameters tuned for each optical inspection system 302 allows for emulation of optical inspection systems. For example, test parameters for a first optical fiber inspection system can be loaded in a second optical fiber inspection system to simulate operation of the first optical fiber inspection system. This can be used to confirm results from an optical fiber inspection system at a remote location.

The data flow between server 306 and each optical fiber inspection system 302 is bi-directional. The optimal test parameters can be tuned and downloaded to each optical fiber inspection system 302 from server 306. Alternatively, test parameters may be tuned at each optical fiber inspection system 302 and then reported to server 306 for future reference.

Each optical fiber inspection system 302 has a local database 303 to store test results and test parameters. Local databases 303 may be implemented using separate devices (e.g., hard drives) or may be implemented using a common storage device accessible without accessing network 304. In the event of a network 304 failure, each optical fiber inspection system 302 operates individually using its local database 303. Once the network 304 is recovered, the stored data in local databases 303 is sent to the server 306 to update database 308. The optical fiber inspection system 302 automatically checks the status of network 304 and determines whether to operate using local database 303.

In addition, test results can be provided from each optical fiber inspection system 302 to server 306 and ultimately database 308. The test results in database 308 may be used to generate reports and be statistically processed to detect manufacturing trends.

As described above, the processes for detecting defects in an image may be executed by a computer forming part of the optical fiber inspection system. The invention may be embodied in the form of computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. Also included may be embodiments in the form of computer program code, for example, whether stored in a storage medium, loaded into and/or executed by a computer, or as a data signal transmitted, whether a modulated carrier wave or not, over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

The invention being thus described, it will be obvious that the same may be varied in many ways. Such variations are not to be regarded as departure from the spirit and scope of the invention, and all such modifications as would be obvious to one skilled in the art are intended to be included within the scope of the following claims.

What is claimed is:

1. A method for detecting defects in an optical fiber, the method comprising:
   obtaining an image of the optical fiber;
   separating a portion of the image for processing;
   determining a blob threshold based on intensities in the portion of the image, to isolate a blob in the portion of the image;
   adjusting characteristics of the portion of the image to enhance detection of the blob;
   identifying the blob in the image referring to the determined blob threshold;
   comparing a characteristic of the blob to blob criteria; and
   failing the optical fiber if the blob criteria is not met.

2. The method of claim 1, wherein the image includes an object and a background, the portion of the image corresponding to the object.

3. The method of claim 2, wherein the object comprises core and cladding of the optical fiber.

4. The method of claim 1, wherein the image includes an object and a background, the portion of the image corresponding to the background.

5. The method of claim 4, wherein the background comprises supporting structure for the optical fiber.

6. The method of claim 1, wherein said determining the blob threshold includes determining a mean intensity of the portion of the image, the blob threshold being based on the mean intensity.

7. The method of claim 6, wherein the blob threshold is determined as $$T_B = \alpha \times I + \beta$$

where $T_B$ is the blob threshold, $I$ is the mean intensity of the portion of the image and $\alpha$ and $\beta$ are scaling constants.

8. The method of claim 1, wherein said adjusting characteristics includes adjusting brightness of the portion of the image.

9. The method of claim 1, wherein said adjusting characteristics includes adjusting contrast of the portion of the image.

10. The method of claim 1, wherein said adjusting characteristics includes adjusting brightness of the portion of the image to a low value and adjusting contrast of the portion of the image to a medium value.

11. The method of claim 1, wherein the characteristic of the blob is blob intensity, the blob criteria including blob intensity.

12. The method of claim 1, further comprising establishing inspection zones in the image, the blob criteria varying for each inspection zone.

13. A storage medium encoded with machine-readable computer program code for detecting defects in an optical fiber, the storage medium including instructions for causing a computer to implement a method comprising:
   obtaining an image of the optical fiber;
   separating a portion of the image for processing;
   determining a blob threshold based on intensities in the portion of the image, to isolate a blob in the portion of the image;
   adjusting characteristics of the portion of the image to enhance detection of the blob;
   identifying the blob in the image referring to the determined blob threshold;
   comparing a characteristic of the blob to blob criteria; and
   failing the optical fiber if the blob criteria is not met.

14. A method for detecting defects in an optical fiber, the method comprising:
   obtaining an image of the optical fiber;
   separating a portion of the image for processing;
   determining a scratch threshold based on intensities in the portion of the image, to isolate a scratch in the portion of the image;
   adjusting characteristics of the portion of the image to enhance detection of the scratch;
   identifying the scratch in the image referring to the determined scratch threshold;
   comparing a characteristic of the scratch to scratch criteria; and
   failing the optical fiber if the scratch criteria is not met.

15. The method of claim 14 wherein the image includes an object and a background, the portion of the image corresponding to the object.

16. The method of claim 15 wherein the object comprises core and cladding of the optical fiber.

17. The method of claim 15 wherein said adjusting characteristics includes adjusting brightness of the portion of the image.

18. The method of claim 15 wherein said adjusting characteristics includes adjusting contrast of the portion of the image.

19. The method of claim 15 wherein said adjusting characteristics includes adjusting brightness of the portion of the image to a medium value and adjusting contrast of the portion of the image to a high value.

20. The method of claim 15 wherein the characteristic of the scratch is scratch intensity, the scratch criteria including scratch intensity.

21. The method of claim 15 further comprising establishing inspection zones in the image, the scratch criteria varying for each inspection zone.

22. The method of claim 15 wherein said detecting the scratch includes morphologically filtering the portion of the image to connect isolated defects, a series of morphologically connected defects along a continuous path being detected as the scratch.

23. The method of claim 14 wherein the image includes an object and a background, the portion of the image corresponding to the background.

24. The method of claim 23 wherein the background comprises supporting structure for the optical fiber.

25. The method of claim 14 wherein said determining the scratch threshold includes determining a mean intensity of the portion of the image, the scratch threshold being based on the mean intensity.

26. The method of claim 25 wherein the scratch threshold is determined as $$T_S \alpha \times I + \beta$$

where $T_S$ is the scratch threshold, I is the mean intensity of the portion of the image and $\alpha$ and $\beta$ are scaling constants.

27. The method of claim 14 wherein the scratch threshold is a light scratch threshold, said determining the scratch threshold including determining a mean intensity of the portion of the image and determining a mean intensity of blobs in the portion of the image, the light scratch threshold being based on the mean intensity of the portion of the image and the mean intensity of the blobs in the portion of the image.

28. The method of claim 27 wherein the scratch threshold is determined as $$T_{LS} \alpha \times I + \gamma \times I_{Blob} + \beta$$

where $T_{LS}$ is the light scratch threshold, I is the mean intensity of the portion of the image, IBM is the mean intensity of the blobs in the portion of the image and $\alpha$, $\gamma$ and $\beta$ are scaling constants.

29. A storage medium encoded with machine-readable computer program code for detecting defects in an optical fiber, the storage medium including instructions for causing a computer to implement a method comprising:

obtaining an image of the optical fiber;

separating a portion of the image for processing;

determining a scratch threshold based on intensities in the portion of the image, to isolate a scratch in the portion of the image;

adjusting characteristics of the portion of the image to enhance detection of the scratch;

identifying the scratch in the image referring to the determined scratch threshold;

comparing a characteristic of the scratch to scratch criteria; and failing the optical fiber if the scratch criteria is not met.

* * * * *